(12) United States Patent
Pietrzkowski

(10) Patent No.: US 11,944,610 B2
(45) Date of Patent: *Apr. 2, 2024

(54) COMPOSITIONS AND METHODS FOR INCREASING ATHLETIC PERFORMANCE

(71) Applicant: VDF Futureceuticals, Inc., Momence, IL (US)

(72) Inventor: Zbigniew Pietrzkowski, Aliso Viejo, CA (US)

(73) Assignee: VDF FutureCeuticals, Inc., Momence, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/888,951

(22) Filed: Aug. 16, 2022

(65) Prior Publication Data

US 2022/0387409 A1 Dec. 8, 2022

Related U.S. Application Data

(63) Continuation of application No. 15/576,809, filed as application No. PCT/US2016/034802 on May 27, 2016, now Pat. No. 11,446,284.

(Continued)

(51) Int. Cl.
*A61K 31/4425* (2006.01)
*A23L 33/105* (2016.01)
(Continued)

(52) U.S. Cl.
CPC ........ *A61K 31/4425* (2013.01); *A23L 33/105* (2016.08); *A23L 33/125* (2016.08);
(Continued)

(58) Field of Classification Search
CPC .............. A61K 31/4425; A61K 9/0053; A61K 9/4858; A61K 31/4439; A61K 31/706;
(Continued)

(56) References Cited

U.S. PATENT DOCUMENTS 8,198,512 B2   6/2012  Goldman et al.
2003/0036565 A1  2/2003  Parkin et al.
(Continued)

FOREIGN PATENT DOCUMENTS

CN   105285634 A    2/2016
DE   102014007762 A1  12/2014
(Continued)

OTHER PUBLICATIONS

Georgiev et al., "Antioxidant Activity and Phenolic Content of Betalain Extracts from Intact Plants and Hairy Root Cultures of hte Red Beetroot "*Beta vilgaris* cv." Detroit Dark Red" Plant Foods Hum Nutrition, 2010, vol. 65.
(Continued)

*Primary Examiner* — Savitha M Rao
*Assistant Examiner* — Andrew P Lee
(74) *Attorney, Agent, or Firm* — Martin Fessenmaier; Umberg Zipser LLP

(57) ABSTRACT

Compositions, methods, and uses are contemplated in which a betalain-containing preparation is administered to a mammal to enhance athletic performance. Most preferably, the preparations are substantially nitrate free and acutely and transiently increase hematocrit, erythropoietin, adrenalin, and beta endorphin, while reducing serum lactate, serum lactate dehydrogenase, heart rate and a rate of perceived exertion.

8 Claims, 5 Drawing Sheets

Related U.S. Application Data

(60) Provisional application No. 62/167,229, filed on May 27, 2015.

(51) Int. Cl.
| | | |
|---|---|---|
| *A23L 33/125* | (2016.01) | |
| *A61K 9/00* | (2006.01) | |
| *A61K 9/48* | (2006.01) | |
| *A61K 31/4439* | (2006.01) | |
| *A61K 31/706* | (2006.01) | |
| *A61K 36/185* | (2006.01) | |
| *A61K 36/21* | (2006.01) | |
| *A61K 47/26* | (2006.01) | |

(52) U.S. Cl.
CPC .......... *A61K 9/0053* (2013.01); *A61K 9/4858* (2013.01); *A61K 31/4439* (2013.01); *A61K 31/706* (2013.01); *A61K 36/185* (2013.01); *A61K 36/21* (2013.01); *A61K 47/26* (2013.01); *A23V 2002/00* (2013.01)

(58) Field of Classification Search
CPC ...... A61K 36/185; A61K 36/21; A61K 47/26; A23L 33/105; A23L 33/125; A23V 2002/00; A61P 43/00; A61P 3/02
See application file for complete search history.

(56) References Cited

U.S. PATENT DOCUMENTS

| | | |
|---|---|---|
| 2010/0047344 A1 | 2/2010 | Lundberg et al. |
| 2010/0076050 A1 | 3/2010 | Pietrzkowski et al. |
| 2011/0190230 A1 | 8/2011 | Pietrzkowski |
| 2013/0108586 A1 | 5/2013 | Lu |
| 2014/0087011 A1 | 3/2014 | Smith |
| 2016/0303176 A1 | 10/2016 | Bailey |

FOREIGN PATENT DOCUMENTS

| | | |
|---|---|---|
| EP | 2420243 A1 | 2/2012 |
| JP | 2011529906 A | 12/2011 |
| WO | 2008094705 A1 | 8/2008 |
| WO | 2010014839 A1 | 2/2010 |
| WO | 2012016018 A4 | 4/2012 |

OTHER PUBLICATIONS

Hoorebeke et al., "Betalaim-Rich Concentrate Supplementation Improves Exercise Performance in Competitive Runners", Sprots, 2016, vol. 4.

Larsen et al., "Dietary Nitrate Reduces Maximal Oxygen Consumption While Maintaining Work Performance in Maximal Exercise", Free Radical Biology and Medicine, 2010, vol. 48.

McIlvenna et al., "Beetroot Juice versus Chard Gel: A Pharmacokinetic and Pharmacodynamic Comparison of Nitrate Bioavailability".

Montenegro et al., "Betalaim-Rich Concentrate Supplementation Improves Exercise Performance and Performance Recovery in Competitive Athletes", Applied Physiological Nutrition Metabolism, 2017, vol. 42.

Murphy et al., "Whole Beetroot Consumption Acutely Improves Running Performance", Journal of the Academy of Nutrition and Dietetics, Apr. 2012, vol. 112, No. 4.

Ormsbee et al., "Beetroot Juice and Exercise Performance, Nutition and Diatery Supplement", 2013, vol. 5.

Ormsbee, M.J., Beetroot juice and exercise performance, Nutrition and Dietary Supplements, Doverpress, Mar. 18, 2019.

Urso et al., "Oxidative Stress, Exercise, and Antioxidant Supplementation", Toxicology, 2003.

Waldenberger et al. "Compositional characteristics of commercial beetroot products and beetroot juice prepared from seven beetroot varieties grown in Upper Austria. Journal of Food Composition and Analysis" (2015) 42, 46-55.

European Patent Office, Summons to Attend Oral Proceedings dated Jun. 14, 2022, 7 pages.

Hashimoto et al., "Prolonged Exercise and Elevation in Lactate Dehydrogenase (LDH)", Bulletin of the Institute of Physical Education, Keio University, 1982; 22(1):19-29.

Hiroyuki, "Sports and Anemia, How should we deal with normal hemoglobin and low ferritin," Bulletin of the Keio University Sports Medicine Research Center, 2012; 6 pgs.

Manabe, Tomohiro, "Measurement of the Cardiopulmonary Function During Exercise," Japanese Journal of Ergonomics, 2016; 52(1):13-18.

Reasons for Submission for Japanese Application No. 2017-561771 submitted on Apr. 7, 2020; 7 pgs.

Takatani, Akira, "Rating of Perceived Exertion during Prolonged Exercise," Bulletin of the Nara University of Education, Natural Sciences, Nov. 2, 19815; 30(2):105-112.

Voet et al., Voet Fundamentals of Biochemistry, 1st Edition, Mar. 1, 20000, 7 pgs., Tokyo Kagaku Dojin Co., Ltd, Tokyo, Japan.

Ymaguchi, et al., "Molecular Adaptation of Lactate Dehydrogenase Isozymes in Leg muscles of Rat by Running-Training," Juntendo University Sports and Health Science Research, 1997; 1:51-57.

COMPOSITIONS AND METHODS FOR INCREASING ATHLETIC PERFORMANCE

This application is a continuation application of our allowed US application with the Ser. No. 15/576,809, which was filed Nov. 25, 2017, and which is a 371 application of PCT/US2016/034802, which was filed May 27, 2016, and which claims priority to U.S. provisional application having Ser. No. 62/167,229, which was filed 27-May-15, and which is incorporated by reference herein.

FIELD OF THE INVENTION

The field of the invention is nutraceutical/pharmaceutical compositions and methods for improving athletic performance, especially to as they relate to compositions that comprise a betalain concentrate that is substantially depleted of nitrate and has a reduced sugar content.

BACKGROUND OF THE INVENTION

Beet root products in various forms (e.g., sold as juice, concentrates, and powders) have recently gained significant attraction among athletes, especially in endurance sports. Most commonly, these products contain significant quantities of inorganic nitrate ($NO_3^-$), which is believed to be reduced by bacteria in the *salvia* into nitric oxide (NO). Clinical studies have suggested positive effects of increased NO levels on muscle efficiency and fatigue resistance (*Journal of Applied Physiology* (1985) 107 (4), 1144-1155, *The Journal of Physiology* 590 (Pt 15), 3575-3583, and *The New England Journal of Medicine* 355 (26), 2792-2793.) and improvements in time-trial endurance tests of hobby athletes (*International Journal of Sport Nutrition and Exercise Metabolism* 22 (1), 64-71; *Journal of the Academy of Nutrition and Dietetics* 112 (4), 548-552). Furthermore, nitrate ingestion reduced resting blood pressure (*Hypertension* 56(2), 274-281) and has been suggested as nutritional agent for the prevention and treatment of hypertension and cardiovascular diseases (Cardiovascular Research 89 (3), 525-532).

Unfortunately, high levels of nitric oxide are thought to correlate with depressive states, which presents a substantial risk factor for dietary use of relatively large quantities of beetroot products (*Journal of Affective Disorders* 63 (1-3), 221-224). Furthermore, recent evidence also suggested that dietary nitrate and nitrite may result in an increased endogenous nitrosation, which may lead to formation of carcinogenic metabolites (*Molecular Nutrition & Food Research* 59 (1), 106-128, *Food Chem Toxicol.* 1997 February; 35(2): 219-24). Still further, many beet root products contain substantial amounts of sugar that will quickly present an undesired caloric intake when beet root products are used at larger quantities. For example, beet root compositional analysis (*Journal of Food Composition and Analysis*, Volume 42, September 2015, Pages 46-55) revealed that the average total sugar content of beet root juice is about 77,000 mg/l total sugar, predominantly sucrose, at a nitrate content of about 1275 mg/l. Notably, the betalain content in beet root is 1100 mg/l with about 700 mg/l betacyanins and 400 mg/l betaxanthins, resulting in a total betalain to total sugar ratio of about 0.0142.

Betalains are pigment extracts that include two classes of compounds: betacyanins, which are red violet, and betaxanthins, which are yellow. The major betalain in red beets (*Beta vulgaris* L.) is betanin, a betacyanin with strong free radical scavenging capacities that is thought to protect cell membranes from lipid peroxidation and heme decomposition. For example, a recent study (*Arch Pharm Res* 2015; 38(4):494-504) showed that betalains, when injected intraperitoneally, had a strong anti-inflammatory effect on carrageenan-induced paw edema and peritonitis in mice. That study also showed reduced production of superoxide anion and the cytokines TNFα and IL-1β, and increased anti-inflammatory IL-10 levels. This study also suggested that betalain supplementation could be utilized in the treatment of inflammation.

In an example of one such suggested use, U.S. Pat. No. 9,060,539 discloses the treatment of osteoarthritis and associated symptoms using betalain containing compositions to improve pain and fatigue associated with osteoarthritis. Notably, the compositions of the '539 patent had a relatively high betalain to sugar ratio and were low in nitrate. Moreover, the compositions of the '539 patent also successfully treated pain and associated fatigue in patients having reduced endurance and strength due to osteoarthritis. However, the betalain containing compositions were not tested on healthy probands or even athletes.

Thus, while numerous compositions and methods of red beet preparations are known in the art, all or almost all of them suffer from disadvantages. Consequently, there is still a need to provide improved compositions and methods for providing low nitrate and low sugar betalain-rich materials to improve physical performances as well as reduce muscle damages.

SUMMARY OF THE INVENTION

The inventor has now discovered that administration of a substantially nitrate free and low sugar betalain-containing preparation can acutely and transiently performance parameters that are associated with an improvement of athletic performance. For example, the inventor has unexpectedly discovered that the compositions presented herein acutely and transiently increased hematocrit, erythropoietin, adrenalin, and beta endorphin, while reducing serum lactate, serum lactate dehydrogenase, heart rate, and the rate of perceived exertion.

In one aspect of the inventive subject matter, the inventor contemplates a method of providing a nutraceutical stimulant to cause acute and transient increase of an exercise enhancing factor of an individual. Such methods will typically include a step of providing a plurality of distinct betalains from a starting material, and a further step of formulating the plurality of distinct betalains into a dosage unit suitable for oral administration. In yet a further step, the dosage unit is administered or caused to be administered to the individual under a protocol effective to increase the exercise enhancing factor of the individual acutely and transiently during or after exercise, wherein the exercise stimulatory factor is selected from the group consisting of adrenalin, hematocrit, erythropoietin, and beta endorphin.

In another aspect of the inventive subject matter, the inventor contemplates a method of reducing an exercise-induced lactate-associated marker of an individual. In such methods, a plurality of distinct betalains from a starting material is provided and formulated into a dosage unit suitable for oral administration. In yet a further step, the dosage unit is administered or caused to be administered to the individual under a protocol effective to reduce the exercise-induced lactate-associated marker, wherein the exercise-induced lactate-associated marker is selected from the group consisting of serum lactate and serum lactate dehydrogenase.

In yet another aspect of the inventive subject matter, the inventor also contemplates a method of reducing an exercise-related physical strain measure of an individual in which a plurality of distinct betalains is provided from a starting material and formulated into a dosage unit suitable for oral administration. In yet a further step, the dosage unit is administered or caused to be administered to the individual under a protocol effective to reduce the exercise-related physical strain measure, wherein the exercise-related physical strain measure is at least one of an exercise-induced increase in heart rate and a rate of perceived exertion (RPE).

In a still further aspect of the inventive subject matter, the inventor also contemplates a method of reducing exercise-induced muscle damage of an individual in which a plurality of distinct betalains is formulated into a dosage unit suitable for oral administration, and in which the dosage unit is administered or caused to be administered to the individual effective to reduce muscle damages of the individual during a physical exercise.

Additionally, the inventor also contemplates in yet another aspect of the inventive subject matter a method of providing a nutraceutical stimulant to reduce a subjective rate of exertion (RPE) of an individual during a physical exercise. In such methods, a plurality of distinct betalains is formulated into a dosage unit suitable for oral administration, and administered or caused to be administered to the individual under a protocol effective to reduce the subjective rate of exertion of the individual during the physical exercise.

Most typically, the dosage unit is substantially nitrate free, and/or further comprises a plurality of sugars, wherein the ratio of the plurality of distinct betalains to the plurality of sugars is at least 0.3. It is further preferred that in the above methods the plurality of distinct betalains is present in the dosage unit in an amount of between 10-500 mg, or in an amount of between 20-100 mg.

While not limiting to the inventive subject matter, it is preferred in at least some embodiments that the plurality of distinct betalains is obtained from an eluate of a hydrophobically modified resin, wherein the starting material is optionally selected from the group consisting of a beet juice, a raw beet or a portion of the raw beet, a beet processing waste liquid, a beet root culture or culture supernatant, a plant material comprising one or more betalains, and a near natural betalain product. With respect to administration it is contemplated that the dosage unit is administered between 2 and 4 hours prior to exercise, or that the dosage unit is administered at least 12 hours prior to exercise.

Therefore, and viewed from a different perspective, the inventor also contemplates use of a betalain-containing composition to acutely and transiently increase at least one of adrenalin, hematocrit, and erythropoietin during or after exercise, wherein the betalain-containing composition is substantially nitrate free.

Alternatively, or additionally, the inventor also contemplates use of a betalain-containing composition to reduce an increase in at least one of exercise induced serum lactate and exercise induced serum lactate dehydrogenase, wherein the betalain-containing composition is substantially nitrate free.

Likewise, the inventor further contemplates use of a betalain-containing composition to reduce an exercise-induced increase in heart rate and a rate of perceived exertion, wherein the betalain-containing composition is substantially nitrate free.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
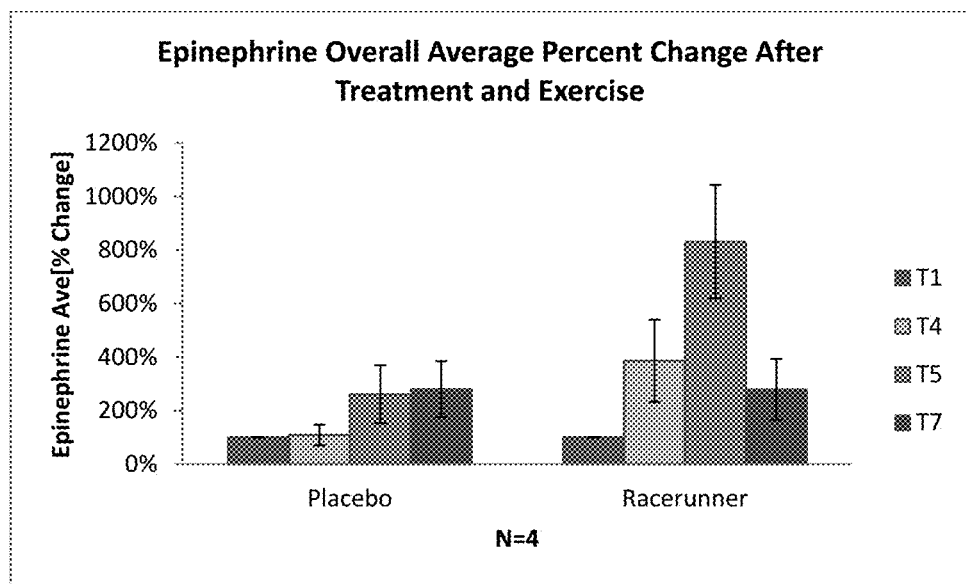
FIG. 1 is a graph depicting test results for blood epinephrine (adrenalin) comparing contemplated formulations (Racerunner) against sugar pill (Placebo). Time points are T1 post administration, no exercise; T4 is post sub-maximal exercise; T5 is post 5 km time trial; T7 is 24 hours after 5 km time trial.

Based on the inventor's earlier discovery that selected betalain-containing products were effective in alleviating symptoms associated with inflammatory conditions (especially symptoms in patients diagnosed with osteoarthritis), the inventor set out to investigate further effects of betalains in a population of healthy individuals, and particularly athletes.

Surprisingly, the inventor now discovered that oral administration of certain betalain-containing compositions can acutely and transiently increase various parameters associated with improved athletic performance while decreasing parameters associated with impaired energy metabolism and muscle damage. Remarkably, the betalain-containing compositions led to substantial improvements in athletic performance while reducing the rate of perceived exertion, all at dosage levels that were well below any known beet root product, and all in the absence of any significant amount of nitrate in these compositions.

Therefore, in one aspect of the inventive subject matter, the inventor contemplates use of various betalain-containing compositions, and especially substantially use of nitrate free compositions with relatively high betalain to sugar ratio to cause acute and transient increase of an exercise enhancing factor (e.g., adrenalin, hematocrit, erythropoietin, beta endorphin, etc.), to reduce one or more exercise-induced lactate-associated markers (e.g., serum lactate and serum lactate dehydrogenase), and to reduce exercise-related physical strain measures (e.g., heart rate and a rate of perceived exertion) and/or exercise-induced muscle damage.

In particularly contemplated methods and uses, the betalain-containing composition typically comprises a plurality of chemically distinct betalains in dried form with relatively low sugar (monosaccharide) content and with substantially reduced nitrate content. Most typically, compositions contemplated herein will have a total betalain (i.e., betaxanthins plus betacyanins) to total sugar (total monosaccharide) ratio of at least 0.05, more typically at least 0.1, even more typically at least 0.5 or at least 1.0, and most typically at least 2.0 while typically having no more than 5 wt %, more typically no more than 2 wt %, and most typically no more than 1 wt % nitrate.

For example, and as is discussed in more detail below, a free-flowing solid betalain-containing composition can be prepared from beet extract or beet juice that comprises a plurality of chemically distinct betalains at a total betalain concentration of at least 2.0 wt % and a betalain to sugar ratio of at least 0.3. Such compositions are solid compositions that are at least 90 wt % (more typically at least 95%, and most typically at least 98%) soluble when dissolved in water at a concentration of at least 50-100 mg/ml. The term "free-flowing" as used herein means that at least 90% of a plurality of separate and individual particles will remain separate and individual in a bulk container when stored over a period of 24 hours at ambient temperature and humidity (75° F. and 50% relative humidity). Thus, a free-flowing small particle powder can be poured from a container in a continuous flow in which substantially the same mass leaves the container in the same time interval. Such properties advantageously allow exact metering of relatively small quantities of betalain-containing compositions into capsules, dragees, or other orally administrable forms at high accuracy. In contrast, all or almost all of the presently known dried betalain materials having betalain concentrations of more than 2 wt % are non-free-flowing materials and will clump together to form aggregates of undefined size and weight and cannot be poured from a container in a continuous flow in which substantially the same mass leaves the container in the same time interval.

Viewed from a different perspective, a preferred betalain-containing composition according to the inventive subject matter will have a total betalain concentration of at least 4.0 wt %, more typically at least 10.0 wt %, even more typically at least 15.0 wt %, and most typically at least 20.0 wt %. It should be noted that the chemical composition of the betalain preparations according to the inventive subject matter is typically a complex composition that includes a plurality of chemically distinct betalains (different betaxanthins and betacyanins). Most preferably, the betalain preparations presented herein have a near natural composition (i.e., no single betacyanin or betaxanthin originally present in the red beet is concentrated or depleted more than 30%, and more typically more than 15-20%, relative to the natural composition). Analysis of betalains and complex compositions can be performed as described by Corke et al (*J Chromatogr Sci.* 2005 October; 43(9):454-60) or Pourrat et al. (*Journal of Food Science* 53 (1), 294-295). Thus, typical preparations will include at least ten, more typically at least twenty, and most typically at least 25 chemically distinct betalains.

For example, most of the betalain-containing compositions presented herein will comprise both betacyanins and betaxanthins, typically with a molar excess of betacyanins relative to betaxanthins (e.g., between 2.5:1 and 1.5:1). However, it should be appreciated that contemplated compositions may also include higher ratios of betacyanins relative to betaxanthins (e.g., between 2.5:1 and 3.5:1, or between 3.5:1 and 5:1, or between 5:1 and 10:1, or even higher). Likewise, contemplated compositions may also include lower ratios of betacyanins relative to betaxanthins (e.g., between 2.5:1 and 1.5:1, or between 1.5:1 and 0.5:1, or between 0.05:1 and 0.5:1, or even lower). Likewise, it should be recognized that where betacyanins and betaxanthins are present, a single species of betacyanin may be combined with a plurality of chemically distinct species of betaxanthins, or that a single species of betaxanthin may be combined with a plurality of chemically distinct species of betacyanins.

For example, suitable betalain-containing compositions can be prepared following a protocol substantially as described in WO 2008/094705, which is incorporated by reference herein. Briefly, commercially available beet juice (about 65 brix; obtained from SVZ International) having a total betalain content of about 0.6 wt % on dry basis was filtered to remove particulates and the filtrate was used without modification for chromatography. The filtrate was passed through a column packed with a hydrophobically modified styrene resin (commercially available as Resin HST-226 from VDF Futureceuticals) at between 1-50 bed volumes per hour at a loading with between 1-20 bed volumes. Pass fractions were discarded, and betalains were eluted from the resin using a mild buffer at slightly basic pH (e.g., 0.1-0.2 M ammonium acetate in water, pH 8.2 to 8.4, at a temperature of 110° F., or 0.1-0.2 M ammonium carbonate in water at pH range 7.0 to 9.0, same temperature). Most typically, slightly basic pH ranges will be between 7.5 and 9.5, and all known buffer systems in that pH range are deemed suitable (basic phosphate buffers, borate buffers, which typically have a potassium, sodium, or ammonium counter cation etc.). It should be appreciated that use of such buffers will not only provide an eluate with relatively high purity and low sugar content, but also reduce nitrate in the eluate to very low levels.

The so obtained eluate was freeze-dried without further modification to a dry product. Samples prepared according to the protocol above had a typical content as provided in the Table below:

| Compound | Quantity |
| --- | --- |
| Total betalains | 27 wt % |
| Betaine | 30 wt % |
| Amino acids | 4 wt % |
| Fiber | 2 wt % |
| Protein | 6 wt % |
| Water | 8 wt % |
| Undetermined | 23 wt % |

It should be noted that so prepared compositions have relatively high nitrogen content as measured by Kjeldahl and Folin-Ciocalteu. Notably, total nitrogen was present in the form of betaine (trimethylglycine), amino acids (which are most likely a mixture of free amino acids and amino acids covalently bound to one or more betalains), free ammonium ions and ammonium ion pairs as well as ammoniated compounds (and especially aminated betalains). Due to the relatively mild and rapid isolation process, it is also contemplated that the so isolated betalains have a relatively large fraction of carboxylated betalains (e.g., at least 50 mol %, more typically at least 80 mol %, most typically at least 90 mol % of total betalains, with 17-decarboxy-forms less than 10 mol %, more typically less than 5 mol %, and most typically less than 3 mol % of total betalains), all or at least some of which may contribute to the observed activities. However, it should be noted that such prepared betalain-containing compositions contain typically less than 5 g of inorganic nitrate per 100 g, more typically less than 1 g, and most typically less than 100 mg of nitrate per 100 g of a final dry composition. Of course, it should be appreciated that nitrate may also be removed using various selective methods, and especially contemplated methods include nitrate specific ion exchange resins, reverse osmosis, electrodialysis, etc. Thus, substantially nitrate free (less than 1 wt %, or less than 0.1 wt %) betalain-containing compositions are particularly contemplated herein.

Moreover, and depending on the particular source material and solvents used, it should be noted that the total betalain to total sugar (monosaccharides) ratio in contemplated compositions is exceptionally high and generally is at least 0.3, more typically at least 0.5, even more typically at least 1.0, and most typically at least 2.0. Viewed from a different perspective, preferred preparations will have a betalain to sugar ratio between 1.0 and 5.0, and even more typically between 2.5 and 4.5. For example, contemplated betalain-containing compositions will therefore have a total sugar content of between 10-20 wt %, more typically between 5-10 wt %, and most typically between 2-5 wt %, or even less. Thus, low sugar contents contemplated herein will be less than 20 wt %, or less than 10 wt %, or less than 5 wt %, or less than 2 wt %, while typically being higher than 0.01 wt %, or higher than 0.1 wt %, or higher than 0.5 wt %. With respect to the remaining sugars in contemplated compositions it should be recognized that the chemical nature will vary and depend on the starting material and work-up. However, most typical remaining sugars include oligo, and/or polysaccharides, sugar alcohols, and pectins (and to some degree monosaccharides). Moreover, it should be appreciated that where the oligo, and/or polysaccharide concentration is to be reduced, enzymatic or fermentative processes may be used to achieve such reduction. Alternatively, or additionally, residual monosaccharides may be removed using various manners known in the art, including ultrafiltration, molecular sieving, and microbial or enzymatic conversion/degradation.

As already noted, numerous raw or starting materials other than red beet juice are also deemed suitable, and especially contemplated materials include raw red beet root or portions thereof (e.g., in solid, macerated, or paste form), red beet processing waste liquids, and red beet root cell cultures and culture supernatants. In still further contemplated aspects, suitable starting materials may also include plant materials that comprise betalains as a natural (or recombinantly produced) pigment. Therefore, betalain containing plants will also include those found in the order of the caryophyllales and selected basidiomycota, and in various cacti (e.g., prickly pear cactus and related plants). Consequently, it should be appreciated that depending on the type of starting material the exact composition of betalains may vary considerably. Additionally, it should be appreciated that the compositions according to the inventive subject matter may also comprise one or more individual isolated or synthetic betalains as sole or supplemental ingredient. However, it is generally preferred that the betalains in the preparation are a complex mixture of betalains with natural or near natural (i.e., deviation of each betalain of less than 10% as compared to natural composition) relative proportions.

In further contemplated aspects, it should be appreciated that while chromatographic isolation as described above is generally preferred, numerous alternative methods to produce betalain-containing compositions are also deemed suitable and include those in which the total betalain concentration is at least 2 wt %, more preferably at least 5 wt %, even more preferably at least 10 wt %, and most preferably at least 20 wt %, typically at a betalain to sugar ratio of at least 0.3, more preferably at least 1.0, and most preferably at least 2.0. For example, stabilized betanidine extracts are prepared using ion exchange chromatography as described in U.S. Pat. No. 4,238,518 or GB patent 1 559 275, while Garin et al. describe in U.S. Pat. No. 4,409,254 a process in which beet root extract is subjected at very low pH to chromatography using a non-ionic resin to so produce a concentrated eluate. Further suitable processes and products are described in U.S. Pat. No. 4,027,042 in which beet juice or beet pulp is subjected to a yeast fermentation and subsequent work-up. Where relatively low yields are acceptable, WO 98/26792 describes various methods of preparing betalain extracts from root pulp, and lyophilized beet is used as starting material, which is subsequently ground, solvent extracted, and subjected to crosslinked dextran chromatography to yield distinct betalain fractions as described in US 2003/0036565.

However, regardless of the particular manner of manufacture, it is generally preferred that the nitrate content of the betalain-containing preparation is typically less than 5 g of inorganic nitrate per 100 g, more typically less than 1 g, and most typically less than 100 mg of nitrate per 100 g of a final dry composition. Moreover, it should be appreciated that while it is generally preferred that the betalain-containing compositions will be dried preparations, gels, and liquid preparations are also deemed suitable for use herein. Such preparations may be further processed to achieve a particular pH, consistency, or concentration of non-betalain components.

It is further contemplated that the preparations according to the inventive subject matter will preferably be solid betalain-containing preparations that may be formulated in numerous manners. For example, suitable formulations include oral formulations (e.g., tablets, capsules, dragees, ready-to-mix formulation, etc.) in which the preparation is the primary ingredient, or formulations in which the preparation is disposed in an edible carrier (e.g., bar, snack, confectionary item, etc.). Alternatively, the betalain-containing preparation may also be a liquid formulation in which the liquid is mixed or encapsulated in (or ready for mixing with) a nutritionally acceptable carrier. For example, suitable liquid formulations may include drinks, syrups, gelatin-encapsulated liquid extracts, oil infusions, soft gels, coatings for capsules, and liquid tinctures. Moreover, and especially where only a single betalain is used as the active ingredient, it is contemplated that the single betalain may be formulated in a pharmaceutically acceptable formulation for oral or parenteral administration. In such case, especially suitable formulations include oral formulations, topical formulations, and even formulations for injection.

As the quantity of betalains administered in a single dosage form are generally very small (e.g., less than 500 mg, more typically less than 250 mg, even more typically less than 100 mg, but higher than 10 mg, and typically higher than 25 mg; e.g., between 25-50 mg, or between 30-100 mg, or between 50 and 250 mg), it should be appreciated that the betalain-containing composition is typically in combination with a carrier. For example, suitable carriers include nutritionally or pharmaceutically acceptable carriers, especially including polysaccharide and mineral carriers.

With respect to the quantity of the betalain-containing preparation administered in a daily dose it is generally preferred that the amount of the preparation is effective to achieve the desired enhancing effect with respect to the performance related parameters. Thus, in most cases suitable amounts will be in the range of between 1 mg and 5 grams, and more typically between 10 mg and 1,000 mg, and most typically between 25 mg and 500 mg. Therefore, and viewed from a different perspective, suitable daily administrations will be at least 1 mg, or at least 10 mg, or at least 25 mg, or at least 100 mg, but no more than 2,000 mg, or no more than 1,000 mg, or no more than 500 mg. Therefore, especially preferred daily dosages of betalains will be between about 0.01 mg/kg to about 10 mg/kg (most preferably 0.1 mg/kg to about 1 mg/kg) body weight.

Most typically, and especially where the composition is administered as a solid, daily dosages will be formulated in an oral composition that will have a total weight of no more than 1,000 mg, or no more than 700 mg, or no more than 500 mg, or no more than 250 mg. Therefore, capsules or tablets (or other orally administrable forms) that provide a daily dosage will have a total weight of between 20-100 mg, or between 100-250 mg, or between 250-500 mg, or between 500-750 mg, or between 750-1,000 mg, depending on inclusion of inert or other functional ingredients (e.g., antioxidants, vitamins, etc.)

While long-term administration is generally preferred, it should be appreciated that administration may extend over at least 3 days, more typically at least 1 week, even more typically at least 1 month, and most typically between 1 month and 6 months. In especially preferred methods and uses, it is contemplated that the compositions contemplated herein are administered in a pre-loading scheme, and are typically administered for at least 2, 3, 5, 7, 14 days prior to an athletic event, and then once between 1 and 12 hour before the athletic event, or between 2 and 6 hours before the athletic event, or between 2 and 4 hours before the athletic event.

Notably, discontinued use of contemplated compositions was not associated with any withdrawal symptoms normally found with energy drinks. In still further unexpected observations, it should also be appreciated (as is discussed in more detail below) that the administration of contemplated compositions will not affect the biological parameters (e.g., adrenalin, hematocrit, erythropoietin, beta endorphins, lactate, LDH, heart rate) in a statistically significant manner during rest or periods of non-exercise (i.e. normal daily activity), but will only affect these parameters acutely during exercise or in a limited time period (e.g., within no more than 12 hours, or within 24 no more than hours, or within no more than 36 hours, or within no more than 36 hours) after exercise in a statistically significant manner. Thus, it should be appreciated that the compositions and methods presented herein will advantageously accentuate benefits associated with exercise (e.g., higher production of beta-endorphins, erythropoietin, epinephrine, and hematocrit) without affecting the individual's physiology when not exercising. Viewed from another perspective, contemplated compositions and methods will advantageously increase exercise performance and mood, satisfaction, and euphoria in an acute and exercise dependent manner. Based on these observations (and other data, not shown), the inventors contemplate that administration of the betalain-containing compositions contemplated herein need not have a preloading schedule, but may be ad hoc (e.g., within 1 hour, or 2 hours, or 3 hours of exercise), or be performed once daily one day (or two or three or four days) before exercise, with the last administration preferably, but not necessarily, at the day of exercise. While not limiting to the inventive subject matter, it is contemplated that while measurable serum quantities of the betalains decrease relatively quickly after single administration (e.g., within 24 hours), the betalains may nevertheless accumulate in the cellular fraction of blood, most likely via intercalation into cell membranes.

Experiments and Examples

The aim of this study was to examine the effects of betalain-containing compositions on performance parameters that are associated with an improvement of athletic performance, including hematocrit, erythropoietin, adrenalin, beta endorphin, serum lactate, serum lactate dehydrogenase, heart rate, and rate of perceived exertion running performance, as well as actual athletic performance. Moreover, the effect of contemplated compositions on muscle soreness and overall fatigue was investigated.

Subjects 15 recreationally competitive, non-elite male runners were recruited from the University of California at Davis campus and local venues to participate in the study. Twelve subjects were needed based on a power analysis (http://hedwig.mgh.harvard.edu/sample_size/j s/js_crossover_quant.html) (power=0.8, significance p=0.05, mean difference (MD)=1.0 min for performance time of supplement versus water in men only and SD of the MD=1.1 min). One subject was excluded during analysis due to noncompliance with the training requirements of the study. Another subject was excluded due to equipment failure during his second exercise trial. Therefore, only 13 of the 15 subjects' data were included in the analysis. Inclusion criteria required that participants run more than 8 miles per week, be nonsmokers, and be generally healthy as determined by a health-history questionnaire. Written informed consent was obtained as approved by the Institutional Review Board of the University of California at Davis.

Experimental Protocols

The first laboratory visit comprised a medical-clearance examination and a maximal exercise test to determine the work intensities for the two subsequent submaximal exercise trials. Seven and fourteen days after the initial screening test, subjects completed two exercise trials. Beginning six days prior to each trial, all subjects ingested a 50 mg capsule of betalain-containing compositions from the root of *Beta Vulgaris* 1. with the sugar and nitrates removed (commercially available as Racerunner™, FutureCeuticals, Momence, IL: 5 kcal, 0.1 mg protein, 1 mg carbohydrate, 0 mg fat, 0.3 mg fiber, 4 mg calcium, 1.4 mg iron, and 25% betalains), or control (oat β-glucans, commercially available as Nutrim®, FutureCeuticals, Momence, IL: 19 kcal, 1 mg protein, 3 mg carbohydrate, 0.4 mg fat, 0.9 mg fiber, 6 mg calcium, 0.3 mg iron), two times per day (30 min prior to breakfast and 30 min prior to dinner). A total of 100 mg of betalain-containing compositions (containing 20 mg of total betalains), or control, were ingested per day. Subjects fasted for 10 h prior to arriving at the laboratory (water was allowed). A 210 kcal snack, consisting of 56% CHO, 22% fat, and 22% protein (Smuckers' Uncrustables®, Strawberry, The T.M. Smucker Company, Orrville, OH) was provided 30 min after supplementation. Since the treatments contained very few calories, the snack was provided to prevent hypoglycemia and to simulate what an athlete would do prior to training or competition. Subjects were then prompted to start exercising 2.5 h post supplementation. All treatments were randomly assigned and double-blinded.

Training and Diet

Seven days of training (type, duration, intensity and miles) and three days of diet were recorded (MyFitnessPal, Inc, San Francisco, CA and a training log) prior to the first trial and followed exactly prior to the second trial to minimize any diet or training effects on exercise performance.

Screening Trial

Subjects reported to the laboratory one week prior to their first experimental trial to complete a medical clearance examination and maximal exercise test. Height and body mass were measured and body composition was determined via a 7-site skin fold test using a Harpenden caliper. Maximal exercise tests were performed on a treadmill (Stairmaster Clubtrack, Vancouver, WA), with the slope set at 1%. After a 5 min warm-up, subjects completed a graded exercise test to exhaustion to determine maximal oxygen consumption (VO2max). The initial speed was 8-11 kmh-1 depending on fitness levels and increased every 2 min by 0.8 kmh-1 until volitional fatigue. A metabolic cart (TrueOne 2400, ParvoMedics, Sandy, UT) was used for metabolic measurements (oxygen consumption (V02), carbon dioxide production (VCO2) and ventilation (VE) rates). The metabolic cart was calibrated prior to each trial with a 3 L syringe at various flow rates (50-400 L/min) and both room air and a standard gas mixture of 16% 02 and 4% CO2. At the end of every 2 min stage, heart rate (HR) via a HR monitor (5410, Polar, Woodbury, NY) and rate of perceived exertion (RPE) using a 10-point scale were measured. Tests were considered maximal if respiratory-exchange ratio (RER) was greater than 1.1 and HRmax was 90% of predicted based on the equation: predHRmax=220-age. From the maximal treadmill test, the speed that elicited 75% of their VO2max was determined and used as the starting workload for the experimental exercise trials. Ventilatory threshold was determined as the speed that caused a systematic increase in the VE/VCO2 ratio.

Experimental Exercise Trials

Subjects reported to the lab between 8:30-10 am in a fasted state and under normal environmental conditions: 21-24° C., 753-768 mmHg and 20-45% relative humidity. Subjects first completed the pre-exercise questionnaires: brief fatigue inventory (BFI), whole body muscle soreness and fatigue by marking a line on a 100 mm visual analogue scale from no pain to extreme pain and not tired to utterly exhausted, and a gastrointestinal discomfort questionnaire (GIDQ). The brief fatigue inventory consisted of nine questions about the severity of fatigue and the effects of fatigue on physical ability and mood. Each question was rated on a scale from 0-10, and the sum of all nine questions was added to get a total fatigue score of 0-90. The GIDQ included 7 categories (abdominal pain, heartburn, regurgitation, bloating, nausea, belching and flatulence) rated as 0 (none), 1 (mild), 2 (moderate), 3 (quite a lot), 4 (severe), 5 (very severe) and 6 (unbearable). After completing the questionnaires, subjects rested quietly on an exam table while a 22G IV catheter was inserted into a forearm vein. Ten minutes after catheter insertions, a pre-exercise 6 mL blood sample, oxygen consumption, RER and HR were obtained. Fifty milligrams of the above betalain-containing composition or placebo was randomly given with 7 ml/kg of water and then subjects rested quietly for 140 minutes. In addition, a standardized meal along with 3 ml/kg of water was ingested 30 min after supplementation. After the rest period, a blood and saliva sample were collected and subjects completed a 10 minute warm up, voided their bladder, and body mass was measured.

Subjects began the 30 min sub-maximal exercise bout 150 min post supplementation. During the first 15 min of sub-maximal exercise, the treadmill speed was set to elicit a work intensity of 75% of VO2max. After 15 min, subjects stopped and straddled the treadmill for 3-5 min while a 6 ml blood sample was collected, 3 ml/kg of water was consumed and the subjects were connected to the metabolic cart. For the second 15 min of the 30 min submaximal exercise bout, speed was adjusted to maintain 75% VO2max. The same treadmill speed increments were used for the subsequent trial. Every 10 min during the 30 min exercise bout, HR and RPE were recorded. A stopwatch was used to monitor rest periods. The same duration and pattern of exercise and rest periods were repeated during the second exercise trial. Immediately after the 30 min sub-maximal exercise bout, 6 ml of blood were collected and the subject consumed 3 ml/kg of water. The subjects then completed a 5 km time trial (TT) (the subjects could adjust the speed, but were blinded to actual speed and HR and could only view the distance completed). Elapsed time, RPE and HR were recorded every 1.6 kilometers during the TT. Immediately after the TT, 6 ml of blood was collected, 3 ml/kg of water was ingested and subjects completed 5 min of active recovery at 4.8 kph. After 15 min of rest, subjects were placed back on the metabolic cart for 10 min to collect recovery VO2, RER and HR. Lastly, a 6 ml blood sample was collected 30 min after completion of the 5 km TT, questionnaires were completed and body mass was recorded. Subjects then ingested another 50 mg of supplement with 3 mL/kg of water. Since betalains are mostly gone from the plasma in about 12 h, an additional capsule was given to maximize the effects of the betalain-containing composition on recovery. Furthermore, 12 and 24 h post-exercise questionnaires were recorded, followed by a 24 h blood draw.

Subjects recorded and followed the same diet and exercise after both exercise trials until the blood draw the next morning.

Blood Analysis

Blood samples were collected in non-heparinized syringes. Blood lactate was determined with a portable analyzer (Lactate Plus, Nova Biomedical, Waltham, MA) and hematocrit was determined using microhematocrit tubes (Statspin, Norwood, MA). Aliquots of 6 mL of blood were divided into two SST tubes. The tubes then sat at room temperature for 30 min and were then centrifuged at 3000 rpm for 10 min. 100 µl of serum was analyzed for serum glucose, creatine kinase (CK), lactate dehydrogenase (LDH) and aspartate aminotransferase (AST) levels using Metlyte 8, Basic Metabolic and Hepatic reagent discs (Piccolo Xpress Chemistry Analyzer, Abaxis, Union City, CA). Cytokines interleukins IL-6, IL-10, IL-13, IL-1β, tumor necrosis factor alpha (TNF-α), granulocyte macrophage colony-stimulating factor GM-CSF and IFN-γ were analyzed using a multiplex immunoassay utilizing magnetically labeled microsphere beads (Millipore HSTCMAG28PMX13BK|MILLIPLEX MAP Human High Sensitivity T Cell Panel, Billerica, MA) for each acquired blood sample. Serum samples were analyzed in duplicate. All samples were stored in a freezer at −80° C. prior to analysis.

Statistical Analysis

Data are presented as means±standard deviation (SD). Repeated measures analysis of variance with Fisher's post hoc analysis determined significant differences (StatView software, Version 5.0.1, SAS Institute Inc., Cary, NC). Significance was accepted at $p \leq 0.05$.

Results

Physical characteristics of the subjects are presented in Table 1. The VO2max values and 5 km TT times placed these runners in the recreationally, but not elite category of competitive runners. The amount of calories consumed and macronutrient proportions from the 3 day diet records (2 days prior to and the day of the exercise trial) were 2388±617 kcal, 45±8% carbohydrate, 21±5% fat and 34±7% protein for BRC (RaceRunner, betalain containing composition as noted above) and 2361±608 kcal, 44±7% carbohydrate, 21±5% fat and 35±6% protein for control. Weekly training volumes were identical between treatments at 24.8±10.2 miles, 6.2±3.4 h and at an average RPE (0-10 scale) of 5.4±1.6.

TABLE 1

Subject physical characteristics

| Variable | mean ± SD | range |
|---|---|---|
| Age, yr | 25.3 ± 5.4 | 18-36 |
| Height, cm | 173.5 ± 4.9 | 163-180 |
| Weight, kg | 70.6 ± 7.9 | 62-90 |
| Body fat, % | 9.6 ± 2.3 | 7.1-13.5 |
| Fat-free mass, kg | 63.7 ± 6.6 | 55-79 |
| Fat mass, kg | 6.8 ± 2.1 | 4.6-11.5 |
| $VO_{2max}$ | | |
| $l \cdot min^{-1}$ | 3.92 ± 0.46 | 3.3-4.8 |
| $ml \cdot kg^{-1} \cdot min^{-1}$ | 55.6 ± 3.7 | 47-63 |

TABLE 1-continued

Subject physical characteristics

| Variable | mean ± SD | range |
|---|---|---|
| $ml \cdot kgFFM^{-1} \cdot min^{-1}$ | 61.5 ± 3.0 | 55-68 |
| Training hours per week | 6.0 ± 3.3 | 3.0-14.0 |
| Running miles per week | 24.8 ± 9.7 | 8.0-38.0 |
| Speed at max, kph | 16.6 ± 1.1 | 14.4-18.4 |
| Speed at Vt, kph | 15.1 ± 1.4 | 12.8-17.6 |
| Maximal Heart Rate, bpm | 194.2 ± 5.8 | 185-204 |
| Maximal Ventilations, $l \cdot min^{-1}$ | 131.1 ± 16.4 | 92-156 |
| Maximal Respiratory Exchange Ratio | 1.1 ± 0.03 | 1.04-1.12 |

Values are means ± SD for 13 men
$VO_2$, oxygen consumption;
Vt, ventilitory threshold,
FFM, fat free mass

Physiological Responses to sub-maximal exercise

Baseline, pre-supplementation HR was 59±6 and 61±7 bpm (p=0.14) for the BRC and control condition, respectively. Baseline VO2 was 0.28±0.06 and 0.28±0.05 l·min-1 (p=0.58) for the BRC and control condition, respectively. Baseline RER was 0.85±0.07 and 0.85±0.05 (p=0.80) for BRC and control conditions, respectively.

Sub-maximal exercise values are reported in Table 2. Speed and % VO2max were similar for the BRC and control trials, which were both below the speed at ventilatory threshold. Although there were no significant differences in VO2 and RER, HR and RPE were 2.8% and 12.9% lower, respectively, for the BRC compared to control. Perceived effort averaged in the moderate to somewhat hard range during the 30 min submaximal exercise bout.

TABLE 2

Physiological Responses during the 30 min sub-maximal exercise bout

| Variable | BRC | Control | p value |
|---|---|---|---|
| Average Speed, kph | 12.2 ± 0.7 | 12.2 ± 0.7 | 1.0 |
| HR, bpm | 165.2 ± 10.8* | 170.0 ± 11.0 | 0.01 |
| $VO_2$, $L \cdot min^{-1}$ | 3.01 ± 0.39 | 3.01 ± 0.33 | 0.99 |
| % $VO_2max$ | 76.9 ± 4.4 | 77.0 ± 3.7 | 0.88 |
| RER | 0.92 ± 0.04 | 0.93 ± 0.04 | 0.09 |
| % energy from CHO | 71.1 ± 15.3 | 76.6 ± 13.6 | 0.09 |
| % energy from Fat | 28.9 ± 15.3 | 23.4 ± 13.6 | 0.09 |
| RPE, 0-10 scale | 3.8 ± 1.5* | 4.4 ± 1.3 | 0.04 |

Values are means ± SD for 13 men
HR, heart rate;
$VO_2$, oxygen consumption,
RER, respiratory exchange ratio;
CHO, carbohydrate;
RPE, rate of perceived exertion;
*significantly different from control Notably, the heart rate was 2.8% lower and the rate of perceived exertion was 10.7% lower for the Betalain treatment using BRC as compared to Placebo. BRC supplementation increased fatty acid oxidation by 19.0% compared to the Placebo trial. Furthermore, the BRC supplementation lowered RPE by 10.6% compared to the Placebo trial. Perceived effort fell into the moderate to hard range during the 30 min submaximal exercise. Blood Lactate level was 2.9±1.6 and 3.3±1.4 mmol·$L^{-1}$ (p≤0.05), with betalain-containing compositions and Placebo treatment respectively.

5K Time Trial

The data from the 5K time trials are presented in Table 3. Betalain supplementation raised 5 k speed by 2.3%, which was matched by a 6.3% drop in RPE. There was also a 2.5% reduction (22 sec) in 5 k-time trial with Betalain supplementation. The 5K times improved in 10 of the 13 subjects with Betalain, 2 of the 13 subjects with Placebo and one subject had the same time for both trials as shown in FIG. 2. Perceived effort fell into the hard to very hard range during the 5K Time Trial.

TABLE 3

Physiological Responses during the 5 km Time Trial

| Variable | BRC | Control | p value |
|---|---|---|---|
| Average Speed, kph | 13.2 ± 1.9* | 12.9 ± 1.8 | 0.04 |
| Time to complete the TT, min | 23.0 ± 4.2* | 23.6 ± 4.0 | 0.04 |
| Average HR, bpm | 176.0 ± 14.5 | 178.3 ± 13.3 | 0.31 |
| RPE, 0-10 scale | 5.9 ± 1.0* | 6.3 ± 1.0 | 0.03 |

Values are means ± SD for 13 men
TT, time trial;
HR, heart rate;
RPE, rate of perceived exertion;
*significantly different from control

Physiological Responses after 30 Minutes of Recovery

Heart rate 30 minutes after completion of the 5K TT was 85.6±9.1 and 91.4±10.3 bpm (p=0.0002), VO2 was 0.33±0.04 and 0.34±0.04 $1 \cdot min^{-1}$ (p=0.21) and RER was 0.76±0.04 and 0.78±0.07 (p=0.09) for the Betalain and Placebo treatments, respectively. Glucose was 88.9±8.8 and 84.3±8.9 (p=0.05), while lactate was 1.9±1.2 and 2.1±1.1 (p=0.21), comparing the Betalain trial to Placebo.

Blood Metabolic Parameters

Serum of four subjects was analyzed for epinephrine (adrenaline) and the results are summarized in FIG. 1. Remarkably, supplementation of athletes with BRC significantly accentuated serum levels of epinephrine across time. While post-administration levels were statistically indistinct, levels at post-submaximal exercise (T4) and post 5 k race (T5) were acutely and strongly increased. Following average values in the Placebo group, max average serum level of adrenaline was 266% increased over T1 followed by 280% increase at T7. For comparison, average % increase of adrenalin at T5 over T1 in the BRC group was 832% followed by 279% increase at T7.

Figure 2A:
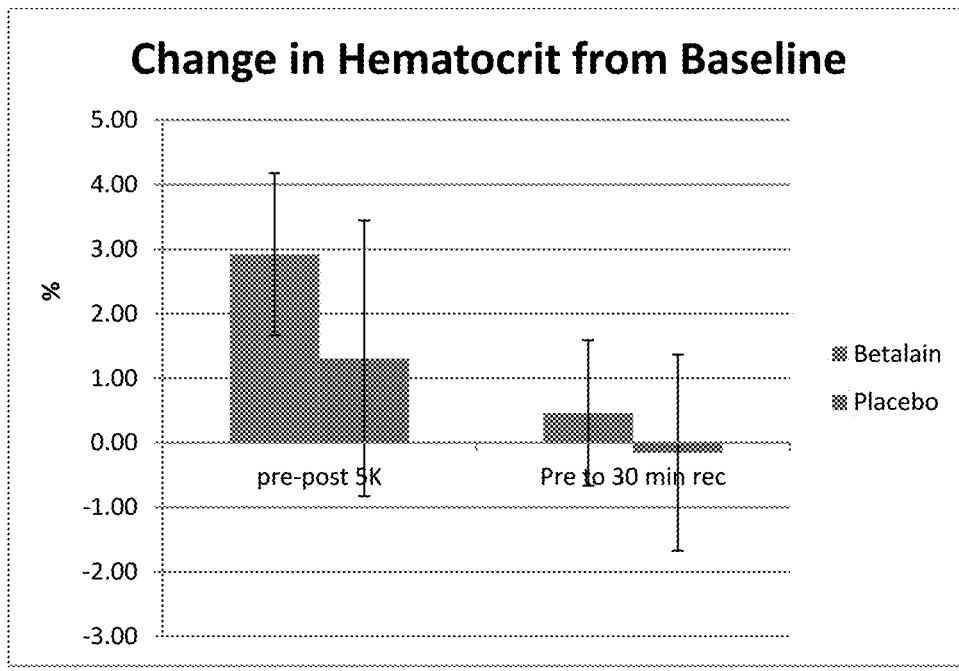
FIG. 2A is a graph depicting test results for hematocrit comparing contemplated formulations (Betalain, left bar) against sugar pill (Placebo, right bar). Pre-post 5 k shows the difference in hematocrit measured between post administration, no exercise, and post 5 km time trial; Pre-30 min rec shows the difference in hematocrit measured between post administration, no exercise, and post sub-maximal exercise.
Figure 2B:
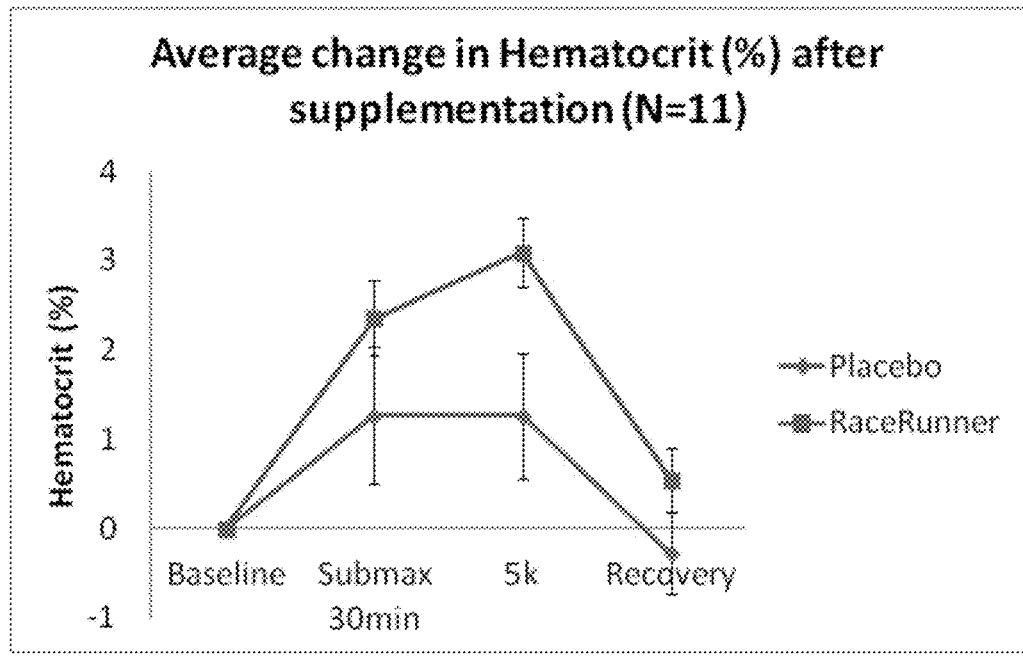
FIG. 2B is a graph depicting test results for hematocrit comparing contemplated formulations (RaceRunner, top line) against sugar pill (Placebo, lower line) over time. Baseline is post administration, no exercise; Submax 30 min is post sub-maximal exercise; 5 k is post 5 km time trial; Recovery is 24 hours after 5 km time trial.

With respect to hematocrit, similar striking and unexpected differences were observed as can be taken from FIG. 2A. Here, the test results for hematocrit comparing contemplated formulations (Betalain, left bar) against sugar pill (Placebo, right bar) over two time intervals. The pre-post 5 k data illustrate the difference in hematocrit measured between the time of post administration (no exercise), and post 5 km time trial. Pre-30 min rec shows the difference in hematocrit measured between the time of post administration (no exercise) and post sub-maximal exercise. As can be readily taken from the graph, hematocrit is acutely and strongly elevated over placebo in both exercise regimens, with the stronger increase associated with more severe exercise. Most remarkably, and at baseline and without exercise, no increase of hematocrit was observed, making this hematocrit boost responsive and sensitive to actual exertion. FIG. 2B illustrates this observation over time. As can be clearly seen from FIG. 2B, the 'area under the curve' for BRC treated athletes is substantially larger than the area for placebo.

Notably, the level of hematocrit was not different between treatments before exercise (44.0±2.7 and 44.6±3.5%, for the Betalain and Placebo treatment, respectively). Hematocrit was similar between treatments during the sub-maximal exercise bout. However, during the 5K TT hematocrit neared significance (p=0.08), with the Betalain treatment being greater than Placebo. Thus, the increase of hematocrit level by Betalain treatment is acute and transient effect, which does not last even half an hour after the exercise. Furthermore, the baseline level of hematocrit is not changed after several days of treatment without exercise. Thus, such acute and transient effect of betalain precludes a possibility that increase of hematocrit with betalain treatment is independent of changes of erythropoietin expression or activity level. The inventors also found that the increase in hematocrit was independent of the blood erythropoietin level of the individual. While not wishing to be bound by any theory or hypothesis, the inventors contemplate that such effect is due to the changes in release capacity of red blood cells or a mechanism preventing the degradation of hematocrit.

Figure 3A:
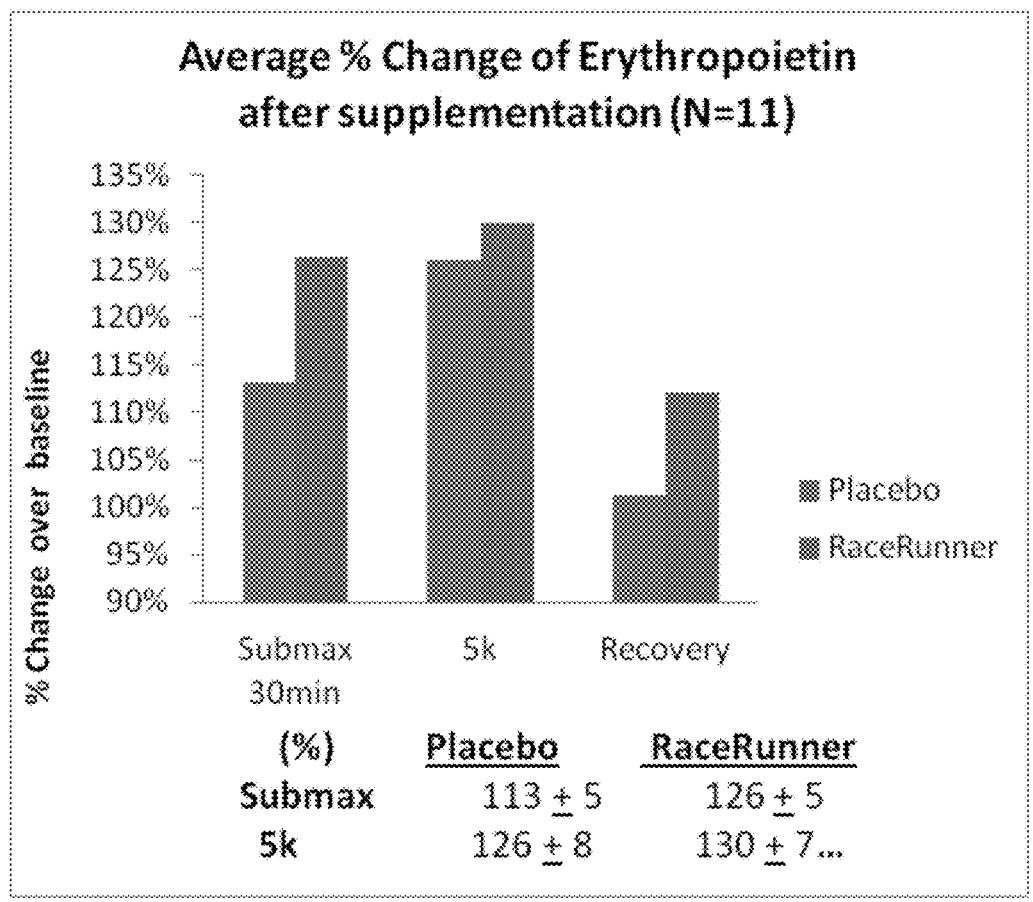
FIG. 3A is a graph depicting test results for erythropoietin comparing contemplated formulations (RaceRunner, right bar) against sugar pill (Placebo, left bar). Submax 30 min is post sub-maximal exercise; 5 k is post 5 km time trial; Recovery is 24 hours after 5 km time trial.
Figure 3B:
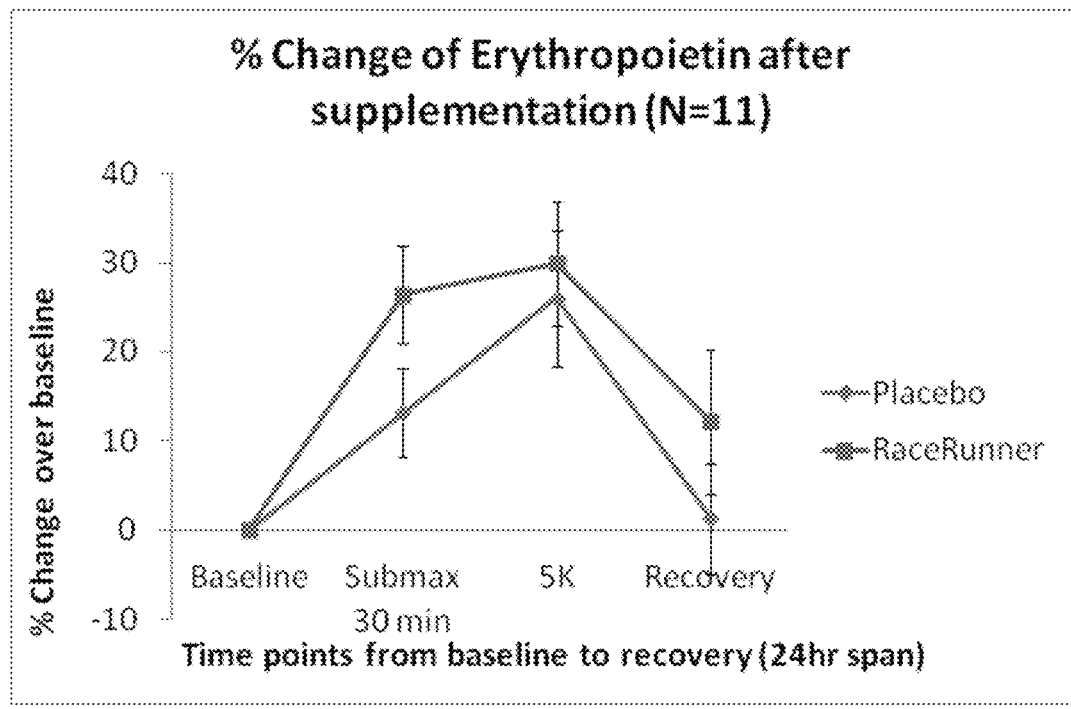
FIG. 3B is a graph depicting test results for erythropoietin comparing contemplated formulations (RaceRunner, top line) against sugar pill (Placebo, lower line) over time. Baseline is post administration, no exercise; Submax 30 min is post sub-maximal exercise; 5 k is post 5 km time trial; Recovery is 24 hours after 5 km time trial.

In a somewhat similar manner, erythropoietin was also identified as being responsive to exercise. FIG. 3A shows exemplary results depicting measured erythropoietin as change over baseline. Here, the increase of erythropoietin is once more acute and substantially stronger for athletes supplemented with BRC. Notably, the increase appeared less sensitive to exercise severity, but more extended in terms of time. While erythropoietin levels in the control group returned to normal after 24 rest, levels in the BRC group maintained at a somewhat elevated level as compared to baseline. This behavior is also reflected in the time course shown in FIG. 3B.

Figure 4:
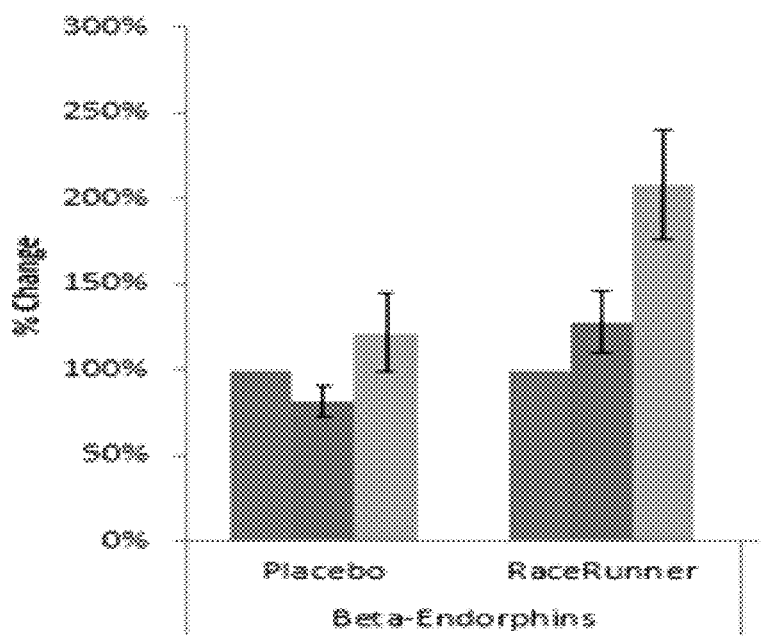
FIG. 4 is a graph depicting changes in beta endorphins comparing contemplated formulations (RaceRunner, right group) against sugar pill (Placebo, left group). Left bar indicates 150 min post administration plus 15 min warm-up and was set to 100%, middle bar is post 5 km time trial, and right bar is 24 hours after time trial.

The effect of the betalain-containing composition and Placebo on blood level of beta-endorphins (BED) in 8 subjects benefiting significantly by reducing time of 5K was assessed. There were no statistically significant differences between any Placebo time-points comparing to corresponding time-points in BRC treated group. However, when analysis was performed to measure % change of beta endorphin levels using levels at 150 minutes after administration of RBC or placebo as 100% mark, the data for post 5 k race and 24 hours after 5 k race resulted in statistically significant elevation of BED (p<0.05 t-test and by Wilcoxon test) comparing to Placebo as is shown in the graph of FIG. 4. Interestingly, blood levels of BED remained elevated in RBC subjects 24 hours after exercise.

Serum glucose significantly decreased from baseline 2.5 h after supplementation and 30 min after the 5 km TT with the control treatment, but was unchanged with BRC supplementation. Serum glucose was not different at baseline, during sub-maximal exercise or after the 5 km TT between treatments, but was 5.2% higher 30 min after the 5 km TT in the BRC treatment compared to control.

Figure 5:
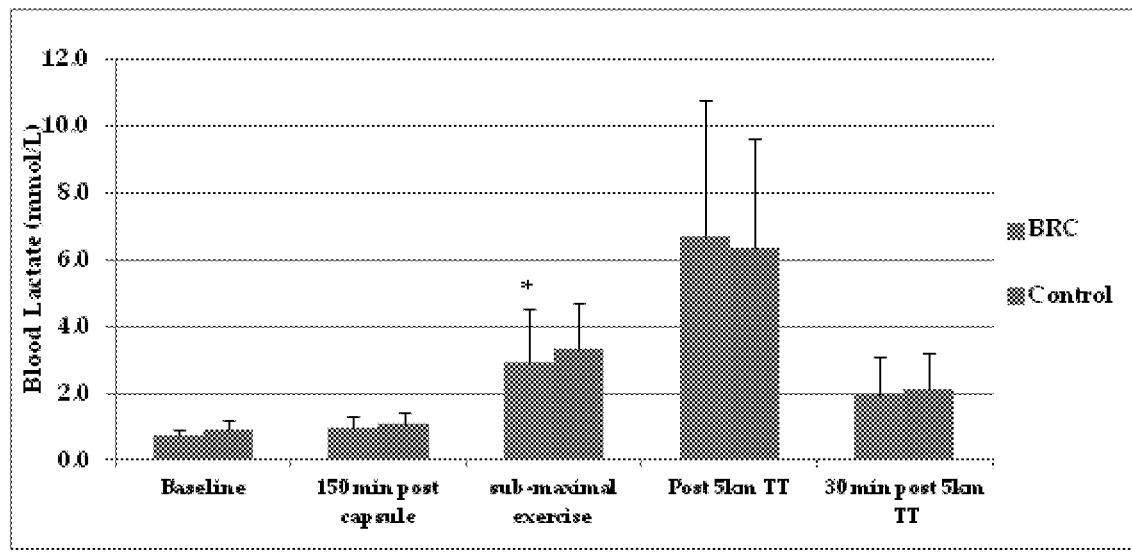
FIG. 5 is a graph depicting changes in blood lactate comparing contemplated formulations (Betalain, left bar) against sugar pill (Placebo, right bar) at various time points as indicated in the graph.

With respect to lactate and further reference to FIG. 5, it was observed that pre-exercise lactate levels were near significant (p=0.06) with the Betalain treatment having higher values. Submaximal exercise induced a significant difference amongst treatments (p=0.05), with lower values with the RBC treatment. However, the 5K TT resulted in no treatment differences in lactate levels (p=0.36) and recovery values were also not different with treatment (p=0.21). Thus, it is contemplated that reduction in lactate is observed during exercise in moderate effect, which may be overridden by lactate accumulation at severe exercise that exceeds lactate clearance.

Blood Muscle Damage Markers

Serum creatine kinase (CK) levels increased with exercise for both treatments, but only remained elevated 24 h after the 5 km TT in the control treatment. These values were just slightly above the reference range of 30-380 U/L. The change in serum CK levels from baseline to immediately after the 5 km TT (103.3±59.4 and 116.7±66.5 U/L, p=0.30 for BRC and control respectively), baseline to 30 min after the 5 km TT (76.9±38.5 and 83.7±50.4 U/L, p=0.54 for BRC and control respectively) and baseline to 24 h after the 5 km TT (63.8±135.0 and 103.4±159.5 U/L, p=0.33 for BRC and control respectively) were not different between treatments.

Figure 6A:
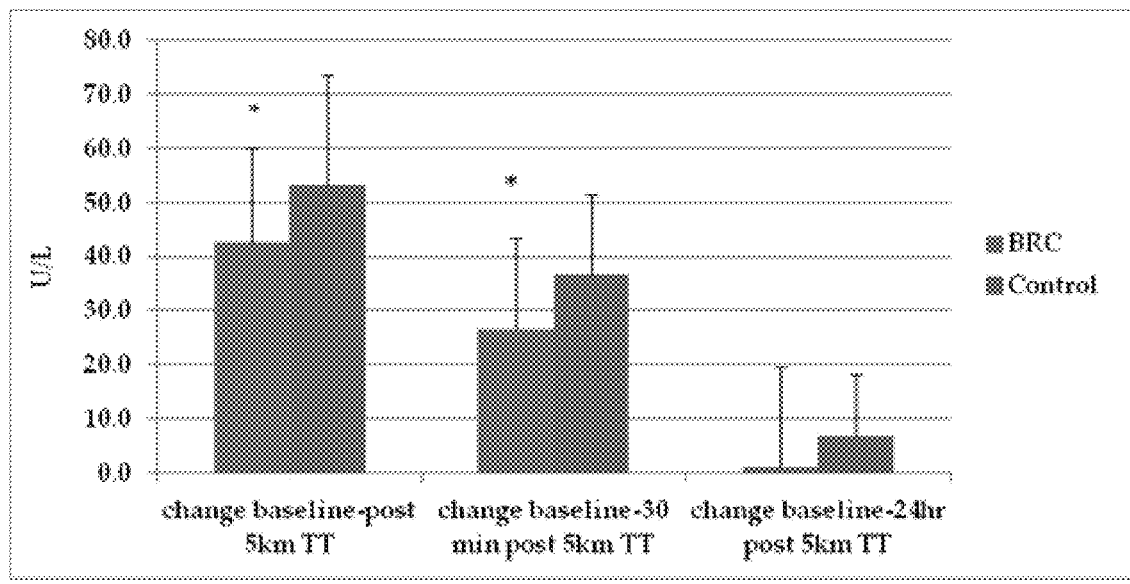
FIG. 6A is a graph depicting changes in LDH comparing contemplated formulations (BRC, left bar) against sugar pill (Control, right bar). Left group indicates changes between post administration, no exercise, and post 5 km time trial, middle group indicates changes between post administration, no exercise, and 30 min post 5 km time trial, and right group indicates changes between post administration, no exercise, and 24 hour post 5 km time trial.
Figure 6B:
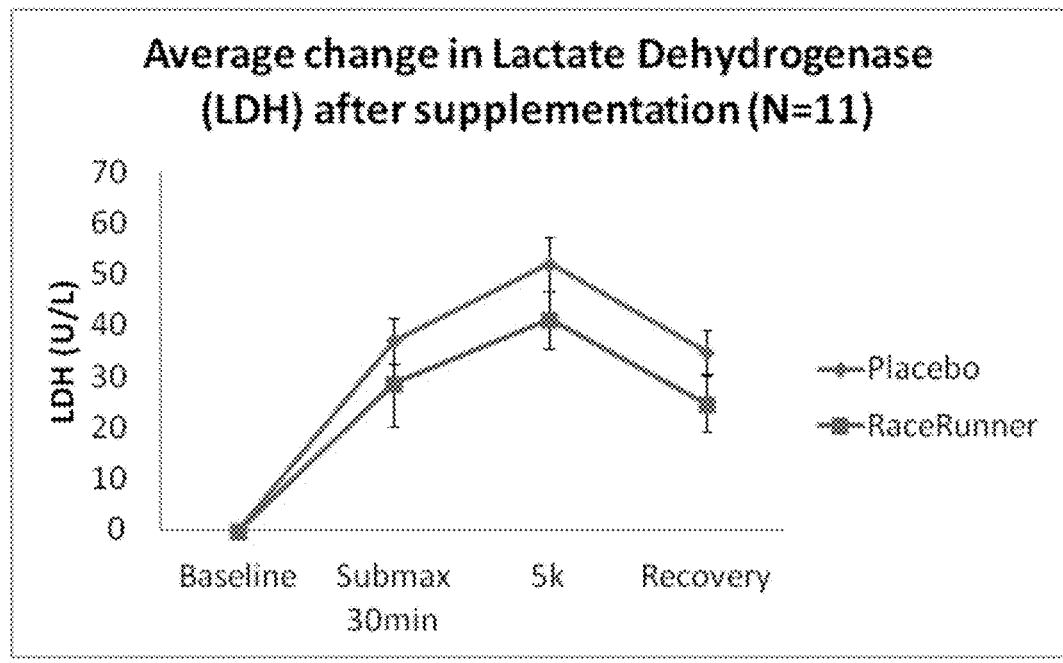
FIG. 6B is a graph depicting changes in LDH comparing contemplated formulations (RaceRunner, lower line) against sugar pill (Placebo, upper line) over time. Baseline is post administration, no exercise; Submax 30 min is post sub-maximal exercise; 5 k is post 5 km time trial; Recovery is 24 hours after 5 km time trial.

Serum lactate dehydrogenase (LDH) levels were not different amongst the trials or when comparing pre-exercise to 24 hours post exercise. However, comparisons of pre-exercise to post 5K TT and pre-exercise to 30 minutes post-exercise yielded near significant changes. Specifically, pre-exercise to post 5K TT LDH were 42.5±17.6 and 53.2±20.4 (p=0.06) comparing Betalain and Placebo trials, respectively. Furthermore, pre-exercise to 30 minutes post-exercise were 26.5±17.0 and 36.5±14.9 (p=0.05) when comparing Betalain and Placebo trials, respectively. FIG. 6A graphically depicts these differences, and it should be readily apparent that muscle damage as characterized by serum LDH activity is acutely and significantly reduced in athletes with RBC treatment. FIG. 6B presents the corresponding time course of LDH activity in serum.

Serum aspartate aminotransferase (AST) levels increased with exercise for both treatments, but only remained elevated 24 h after the 5 km TT in the control treatment. These values were just slightly above the reference range of 11-38 U/L. The change in serum AST levels from baseline to after the 5 km TT (6.7±3.3 and 5.9±2.5 U/L, p=0.46 for BRC and control respectively), baseline to 30 min after the 5 km TT (4.8±3.0 and 4.2±2.5 U/L, p=0.59 for BRC and control respectively) and baseline to 24 h after the 5 km TT (3.2±7.1 and 4.9±8.2 U/L, p=0.21 for BRC and control respectively) were not different between treatments.

Whole body muscle soreness at baseline (11.7±9.3 and 11.1±15.1 mm out of 100 mm; p=0.83 for BRC and control respectively) was not different between treatments. Muscle soreness increased after the 5 km TT, but was not different between treatments (25.4±9.6 and 28.7±13.1 mm out of 100 mm; p=0.40 for BRC and control respectively). Whole body muscle soreness remained elevated at 12 (21.5±14.1 and 20.2±14.4 mm out of 100 mm; p=0.76 for BRC and control respectively) and 24 hours (21.4±13.1 and 15.8±14.5 mm out of 100 mm; p=0.15 for BRC and control respectively) after the 5 km TT, but was not different by treatment. Whole body fatigue at baseline (19.1±13.4 and 15.6±14.5 mm out of 100 mm; p=0.25 for BRC and control respectively) was not different between treatments. Whole body fatigue increased after the 5 km TT, but was not different between treatments (46.5±16.0 and 45.6±19.4 mm out of 100 mm; p=0.82 for BRC and control respectively). Whole body fatigue remained elevated at 12 hours after the 5 km TT (26.85±15.2 and 31.8±17.5 mm out of 100 mm; p=0.34 for BRC and control respectively), but decreased to baseline at 24 hours after the 5 km TT (23.6±16.9 and 22.5±15.2 mm out of 100 mm; p=0.79 for BRC and control respectively) for both treatments and was not different between treatments.

Markers of Inflammation

Serum pro-inflammatory cytokine levels are indicated in Table 4. There were no significant differences between treatments except for IL-1β where levels were significantly lower 30 min after the 5 km TT after the BRC treatment.

TABLE 4

| | Serum Cytokine Response to Exercise (pg/ml) | | | |
|---|---|---|---|---|
| Variable | | Baseline | Post 5 km TT | 30 min Post 5 km TT | 24 hr Post 5 km TT |
| IL-2 | BRC | 1.8 ± 1.6 | 2.2 ± 1.9# | 2.1 ± 1.9 | 2.1 ± 1.7 # |
| | Control | 2.1 ± 1.9 | 2.5 ± 2.1 | 2.6 ± 2.1 | 2.0 ± 1.6 |
| IL-5 | BRC | 1.2 ± 0.9 | 1.5 ± 1.1 | 1.3 ± 1.0 | 1.4 ± 1.1 |
| | Control | 1.1 ± 0.9 | 1.6 ± 1.2# | 1.6 ± 1.5 | 1.3 ± 1.0 |
| IL-6 | BRC | 1.1 ± 1.1 | 2.2 ± 1.3# | 1.9 ± 1.3# | 1.2 ± 1.2 |
| | Control | 1.2 ± 1.3 | 2.4 ± 1.4# | 2.1 ± 1.4# | 1.1 ± 1.2 |
| IL-7 | BRC | 4.8 ± 3.8 | 5.7 ± 4.2 | 5.9 ± 4.1# | 5.8 ± 4.0 # |
| | Control | 5.2 ± 4.3 | 6.1 ± 4.3# | 5.8 ± 4.3# | 5.1 ± 3.3 |
| IL-8 | BRC | 3.7 ± 1.3 | 4.6 ± 1.6# | 4.7 ± 1.4# | 4.0 ± 1.3 # |
| | Control | 3.8 ± 1.1 | 4.8 ± 1.1# | 4.9 ± 1.4# | 4.0 ± 1.4 |
| IL-10 | BRC | 7.1 ± 6.2 | 10.5 ± 8.6# | 12.2 ± 7.6# | 7.7 ± 6.3 |
| | Control | 6.7 ± 6.1 | 10.2 ± 7.7# | 10.9 ± 7.8# | 6.7 ± 5.9 |
| IL-12 | BRC | 1.7 ± 1.1 | 2.7 ± 1.9# | 2.1 ± 1.8 | 2.1 ± 1.7 |
| | Control | 2.2 ± 1.9 | 2.5 ± 2.1# | 2.6 ± 2.1 | 2.0 ± 1.6 |
| IL-13 | BRC | 4.2 ± 3.2 | 5.1 ± 3.9# | 4.6 ± 3.4 | 4.5 ± 3.4 |
| | Control | 4.3 ± 3.3 | 5.2 ± 4.2# | 4.7 ± 3.7# | 4.4 ± 3.5 |
| IL-1β | BRC | 0.58 ± 0.46 | 0.72 ± 0.45 | 0.75 ± 0.59* | 0.67 ± 0.51 |
| | Control | 0.71 ± 0.60 | 0.90 ± 0.75 | 0.87 ± 0.63 | 0.68 ± 0.38 |
| TNF-α | BRC | 2.8 ± 1.0 | 4.0 ± 1.4# | 3.7 ± 1.2# | 3.2 ± 1.0 # |
| | Control | 2.9 ± 1.1 | 4.1 ± 1.2# | 4.0 ± 1.5# | 3.0 ± 0.7 |
| GM-CSF | BRC | 36.8 ± 39.3 | 44.6 ± 50.0 | 43.5 ± 44.2 | 38.0 ± 39.4 |
| | Control | 42.7 ± 52.5 | 48.0 ± 54.4# | 43.2 ± 45.1 | 37.3 ± 37.7 |
| IFN-γ | BRC | 7.5 ± 5.3 | 11.7 ± 7.2# | 10.0 ± 6.7# | 9.6 ± 6.5 # |
| | Control | 8.3 ± 7.7 | 11.9 ± 8.3# | 10.0 ± 7.8# | 8.1 ± 5.5 |

Values are means ± SD for 13 men;
BRC, betalain rich concentrates;
, significantly different from baseline,
*, significantly different from control,
p ≤ 0.05

Heart Rate

Figure 7:
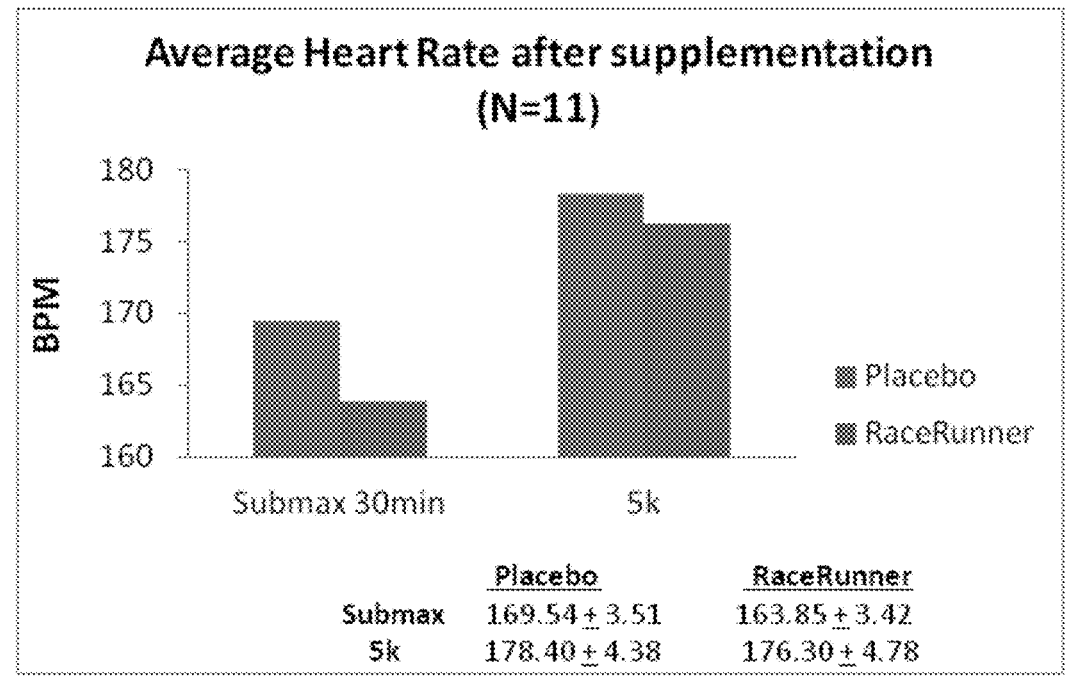
FIG. 7 is a graph depicting heart rates comparing contemplated formulations (RaceRunner, right bar) against sugar pill (Placebo, left). Submax 30 min is post sub-maximal exercise; 5 k is post 5 km time trial.

When considering effects of the betalain-containing compositions on heart rate, the inventor discovered that the average heart rate during submaximal exercise and the 5 k time trial were reduced for athletes treated with RBC as is shown in FIG. 7. The heart rate was significantly lower with Betalain supplementation during the submaximal trial (p=0.01), suggesting that NO-induced vasodilation led to a reduction in afterload and therefore reduced work on the heart. Chards, which contain Betalains, have been shown to reduce acetylcholinesterase (AchE) activity. Meanwhile, inhibition of AchE has been shown to enhance vagal-mediated reductions in HR and endothelial cholinergic-mediated NO production. A reduction in afterload is supported by a study, which found that both acute (1 day) and chronic (6 day) 5.5 mmol/day nitrate supplementation was associated (r=−0.71, p<0.05) with reduced systolic blood pressure (mean=6 mmHg) during cycling in healthy young men. Lastly, the decrease in HR seen in this study was not causative to hydration status, as there were no differences in hematocrit during exercise and there were no differences in body weight lose pre- to post-exercise between Betalains and Placebo.

Reduced afterload also translates to a reduced need for sympatho-adrenal output, which is supported by lower lactate levels during exercise with Betalain supplementation. Lactate production is a result of catecholamine-induced mobilization of muscle glycogen or blood glucose. Beetroot supplementation in rats resulted in a significant decrease in plasma lactate levels during treadmill exercise, indicating lower carbohydrate utilization. There was a trend (p=0.09) toward lower respiratory exchange ratios during the submaximal exercise bout with Betalain supplementation in our study, suggesting greater fatty acid oxidation and less carbohydrate oxidation. Power analysis revealed that 20 subjects would be enough to see a significant difference in RER. 9 of 13 subjects had lower RER values with Betalain, 3 had lower RER with Placebo and 1 had similar values for both treatments.

Corroborating a shift in energy substrate utilization, others showed that lactate levels were significantly reduced (p<0.05) in exercising rats fed 1 mmol kg$^{-1}$ day$^{-1}$. Furthermore, they found an increase in blood flow to type II muscle fibers (r=0.74, p<0.01), thus reducing reliance on glycolysis and shifting metabolism towards oxidation. More interestingly, a study has showed that the AchE inhibitor, pyridostigmine, reduces skin blood flow during cycling exercise at 55% VO2max. Acetylcholine-induced shunting of systemic blood to cutaneous circulations reduces oxygen availability to working muscles and therefore has the potential to reduce exercise performance. Therefore, AchE inhibition from Betalain supplementation, as elucidated, could potentially improve muscle oxygenation by redirecting cardiac output and fostering an environment that supports fatty acid metabolism.

Betalains have been shown to reduce pain and fatigue in patients suffering from osteoarthritis. Surprisingly, betalain-containing compositions have now also been demonstrated to improve various parameters associated with exercise, particularly where such improvement was acute and transient, and observed only during and after exercise. Indeed, the inventor discovered that the betalain composition disclosed herein acutely and transiently increased hematocrit, erythropoietin, adrenalin, and beta endorphin, while reducing serum lactate, serum lactate dehydrogenase, heart rate, and the rate of perceived exertion. Finally, it should be noted that the benefits of betalain-containing compositions will apply to both aerobic exercises (e.g., running/jogging, swimming, cycling, and walking, etc.) as well as anaerobic exercises (e.g., weight lifting, sprinting, jumping, or any exercise that consists of short exertion, high-intensity movement, etc.).

Absorption

Serum concentration of various betalains was tested after oral administration of 100 mg of contemplated betalain-containing composition. As Table 5 below indicates, different forms of betalains had substantial and measurable increase in serum at about 180 minutes post administration.

| t [min] | Bt | 17-dBt | lBt | 17-dlBt |
|---|---|---|---|---|
| 60 | 22112 | 16797 | 18946 | 12436 |
| 120 | 28922 | 20090 | 21372 | 13938 |
| 180 | 122565 | 99401 | 117093 | 100612 |

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or the claims refer to at least one of something selected from the group consisting of A, B, C . . . and N, the text should be interpreted as requiring only one element from the group, not A plus N, or B plus N, etc.

What is claimed is:

1. A method of providing a nutraceutical composition to improve mood in an individual, comprising:
   providing a plurality of distinct betalains from a starting material;
   formulating the plurality of distinct betalains into a dosage unit suitable for oral administration;
   administering or causing to administer the dosage unit to the individual in an amount effective to improve mood in an acute and exercise dependent manner.

2. The method of claim 1, wherein the dosage unit is substantially nitrate free.

3. The method of claim 1, wherein the dosage unit further comprises a plurality of sugars, and wherein a ratio of the plurality of distinct betalains to the plurality of sugars is at least 0.3.

4. The method of claim 2, wherein the dosage unit further comprises a plurality of sugars, and wherein a ratio of the plurality of distinct betalains to the plurality of sugars is at least 0.3.

5. The method of claim 1, wherein the plurality of distinct betalains is present in the dosage unit in an amount of between 10-500 mg.

6. The method of claim 1, wherein the plurality of distinct betalains is present in the dosage unit in an amount of between 20-100 mg.

7. The method of claim 1, wherein the plurality of distinct betalains is obtained from an eluate of a hydrophobically modified resin.

8. The method of claim 7, wherein the hydrophobically modified resin is loaded with a starting material selected from the group consisting of a beet juice, a raw beet or a portion of the raw beet, a beet processing waste liquid, a beet root culture or culture supernatant, a plant material comprising one or more betalains, and a near natural betalain product.

* * * * *